(12) United States Patent
Thompson et al.

(10) Patent No.: US 8,696,729 B2
(45) Date of Patent: *Apr. 15, 2014

(54) IMPLANT DELIVERY SYSTEM WITH MARKER INTERLOCK

(75) Inventors: Paul J. Thompson, Minnetonka, MN (US); Nathan T. Lee, Golden Valley, MN (US)

(73) Assignee: Covidien LP, Mansfield, MA (US)

( * ) Notice: Subject to any disclaimer, the term of this patent is extended or adjusted under 35 U.S.C. 154(b) by 725 days.

This patent is subject to a terminal disclaimer.

(21) Appl. No.: 12/059,582

(22) Filed: Mar. 31, 2008

(65) Prior Publication Data

US 2009/0069879 A1   Mar. 12, 2009

Related U.S. Application Data

(63) Continuation of application No. 10/982,537, filed on Nov. 4, 2004, now abandoned, which is a continuation of application No. 10/286,403, filed on Nov. 1, 2002, now Pat. No. 6,814,746.

(51) Int. Cl.
*A61F 2/06* (2013.01)

(52) U.S. Cl.
USPC ........................................................ 623/1.11

(58) Field of Classification Search
USPC ................ 606/108, 191–198; 623/1.11, 1.12, 623/1.13, 1.15, 1.16–1.18, 1.34
See application file for complete search history.

(56) References Cited

U.S. PATENT DOCUMENTS

| 264,502 | A | 9/1882 | Woolson |
|---|---|---|---|
| 3,902,501 | A | 9/1975 | Citron et al. |
| 4,051,592 | A | 10/1977 | Briles |
| 4,531,243 | A | 7/1985 | Weber et al. |
| 4,572,186 | A | 2/1986 | Gould et al. |
| 4,733,665 | A | 3/1988 | Palmaz |
| 4,768,507 | A | 9/1988 | Fischell et al. |
| 4,828,566 | A | 5/1989 | Griss |
| 4,913,141 | A | 4/1990 | Hillstead |
| 5,026,377 | A | 6/1991 | Burton et al. |
| 5,080,674 | A | 1/1992 | Jacobs et al. |
| 5,104,404 | A | 4/1992 | Wolff |
| 5,306,250 | A | 4/1994 | March et al. |

(Continued)

FOREIGN PATENT DOCUMENTS

| DE | 299 04 817 | 7/1999 |
|---|---|---|
| EP | 0 709 068 | 5/1996 |

(Continued)

OTHER PUBLICATIONS

Brochure entitled "memotherm FLEXX.TM. Vascular Stent" by Angiomed GmbH & Co. Medizintechnik KG, 3 pages (Sep. 1999).

(Continued)

*Primary Examiner* — Darwin Erezo
*Assistant Examiner* — Amy Shipley
(74) *Attorney, Agent, or Firm* — Alana T. Bergman, Esq.

(57) ABSTRACT

An implant delivery system is disclosed. The delivery system includes an elongated member having an implant mounting location. A self-expandable implant is mounted at the implant mounting location. The implant is held in a compressed orientation by a retractable sheath. An interlock structure prevents the implant from deploying prematurely as the sheath is retracted. The interlock structure includes radio-opaque markers that identify the position of the implant.

10 Claims, 8 Drawing Sheets

(56) References Cited

U.S. PATENT DOCUMENTS

| | | | |
|---|---|---|---|
| 5,366,473 A | 11/1994 | Winston et al. | |
| 5,443,520 A | 8/1995 | Zweymuller et al. | |
| 5,480,423 A | 1/1996 | Ravenscroft et al. | |
| 5,484,444 A | 1/1996 | Braunschweiler et al. | |
| 5,556,413 A | 9/1996 | Lam | |
| 5,591,172 A | 1/1997 | Bachmann et al. | |
| 5,607,442 A | 3/1997 | Fischell et al. | |
| 5,632,771 A | 5/1997 | Boatman et al. | |
| D380,831 S | 7/1997 | Kavteladze et al. | |
| 5,695,499 A | 12/1997 | Helgerson et al. | |
| 5,725,570 A * | 3/1998 | Heath | 623/1.2 |
| 5,725,572 A | 3/1998 | Lam et al. | |
| 5,733,325 A * | 3/1998 | Robinson et al. | 623/1.11 |
| 5,741,327 A | 4/1998 | Frantzen | |
| 5,759,186 A | 6/1998 | Bachmann et al. | |
| 5,800,508 A | 9/1998 | Goicoechea et al. | |
| 5,800,526 A | 9/1998 | Anderson et al. | |
| 5,817,102 A | 10/1998 | Johnson et al. | |
| 5,824,042 A | 10/1998 | Lombardi et al. | |
| 5,824,077 A | 10/1998 | Mayer | |
| 5,954,729 A | 9/1999 | Bachmann et al. | |
| 6,004,328 A | 12/1999 | Solar | |
| 6,022,374 A | 2/2000 | Imran | |
| 6,066,168 A | 5/2000 | Lau et al. | |
| 6,077,295 A | 6/2000 | Limon et al. | |
| 6,077,297 A * | 6/2000 | Robinson et al. | 623/1.11 |
| 6,120,522 A | 9/2000 | Vrba et al. | |
| 6,129,754 A | 10/2000 | Kanesaka et al. | |
| 6,132,460 A | 10/2000 | Thompson | |
| 6,132,461 A | 10/2000 | Thompson | |
| 6,203,569 B1 | 3/2001 | Wijay | |
| 6,214,036 B1 * | 4/2001 | Letendre et al. | 623/1.11 |
| 6,235,050 B1 | 5/2001 | Quiachon et al. | |
| 6,267,783 B1 | 7/2001 | Letendre et al. | |
| 6,315,790 B1 | 11/2001 | Gerberding et al. | |
| 6,334,871 B1 | 1/2002 | Dor et al. | |
| 6,395,017 B1 | 5/2002 | Dwyer et al. | |
| 6,402,777 B1 | 6/2002 | Globerman et al. | |
| 6,409,752 B1 | 6/2002 | Boatman et al. | |
| 6,623,518 B2 * | 9/2003 | Thompson et al. | 623/1.11 |
| 6,776,791 B1 * | 8/2004 | Stallings et al. | 623/1.11 |
| 6,814,746 B2 * | 11/2004 | Thompson et al. | 623/1.11 |
| 6,936,058 B2 | 8/2005 | Forde et al. | |
| 8,257,427 B2 | 9/2012 | Andersen et al. | |
| 2001/0001317 A1 | 5/2001 | Duerig et al. | |
| 2002/0143386 A1 * | 10/2002 | Davila et al. | 623/1.15 |

FOREIGN PATENT DOCUMENTS

| | | |
|---|---|---|
| EP | 0 775 470 | 5/1997 |
| EP | 0 847 733 | 6/1998 |
| EP | 0 800 800 | 7/1998 |
| EP | 0 894 481 | 2/1999 |
| EP | 0 895 760 | 2/1999 |
| EP | 0 679 372 | 7/1999 |
| EP | 0 943 302 | 9/1999 |
| EP | 0 945 107 | 9/1999 |
| EP | 0 947 179 | 10/1999 |
| EP | 0 947 179 | 12/1999 |
| EP | 1 000 590 | 5/2000 |
| EP | 1 086 665 | 3/2001 |
| EP | 1 157 673 | 11/2001 |
| EP | 1 212 989 | 6/2002 |
| GB | 1 205 743 | 9/1970 |
| WO | WO 95/03010 | 2/1995 |
| WO | WO 97/33534 | 9/1997 |
| WO | WO 99/30643 | 6/1999 |
| WO | WO 00/15151 | 3/2000 |
| WO | WO 00/64375 | 11/2000 |
| WO | WO 02/15820 | 2/2002 |
| WO | WO 02/26281 | 4/2002 |
| WO | WO 02/32496 | 4/2002 |
| WO | WO 02/067782 | 9/2002 |
| WO | WO 02/078762 | 10/2002 |
| WO | WO 03/022178 | 3/2003 |

OTHER PUBLICATIONS

European Search Report for EP 03 07 8460 dated Jan. 23, 2004 (3 pgs.).

* cited by examiner

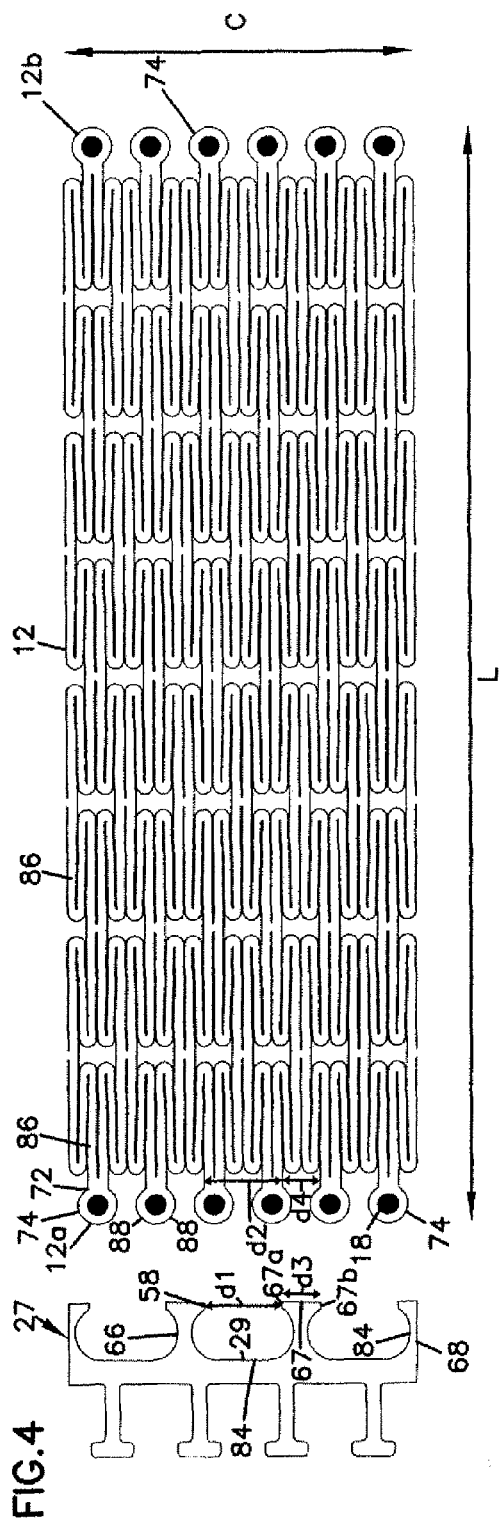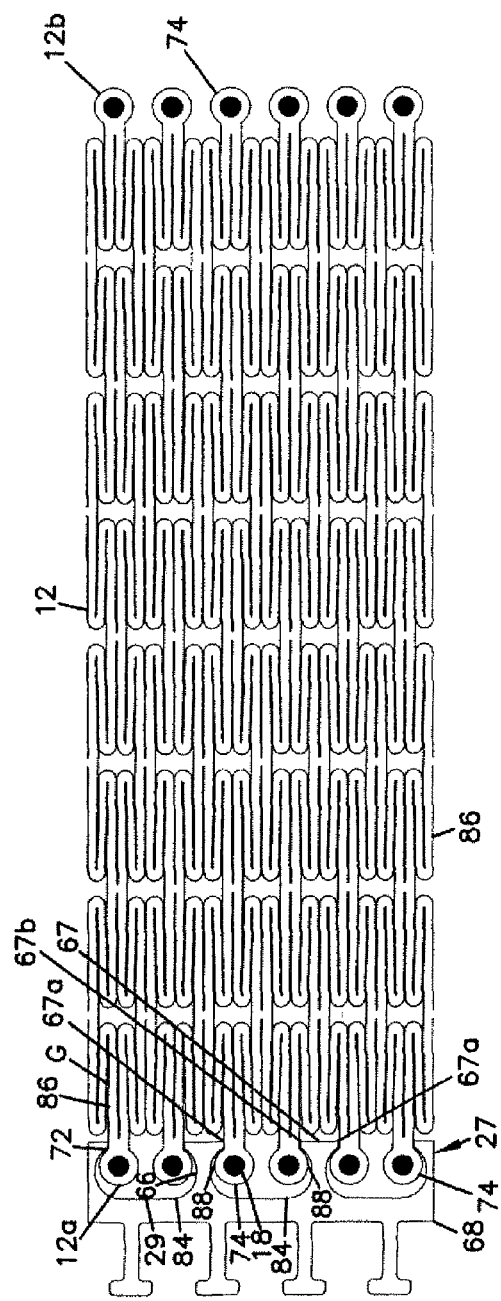

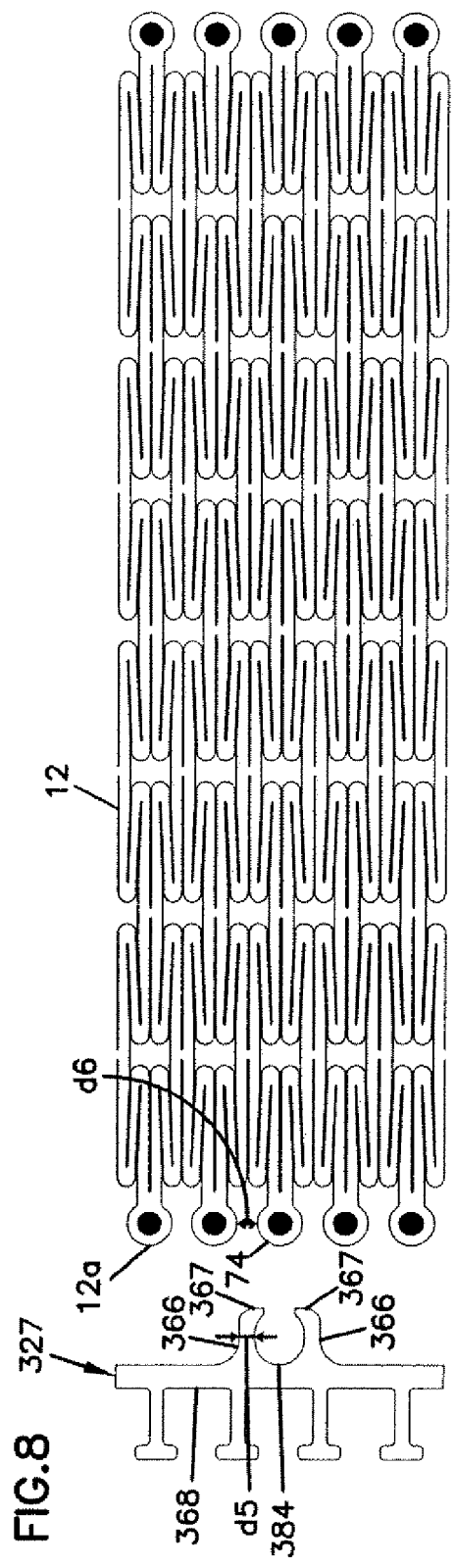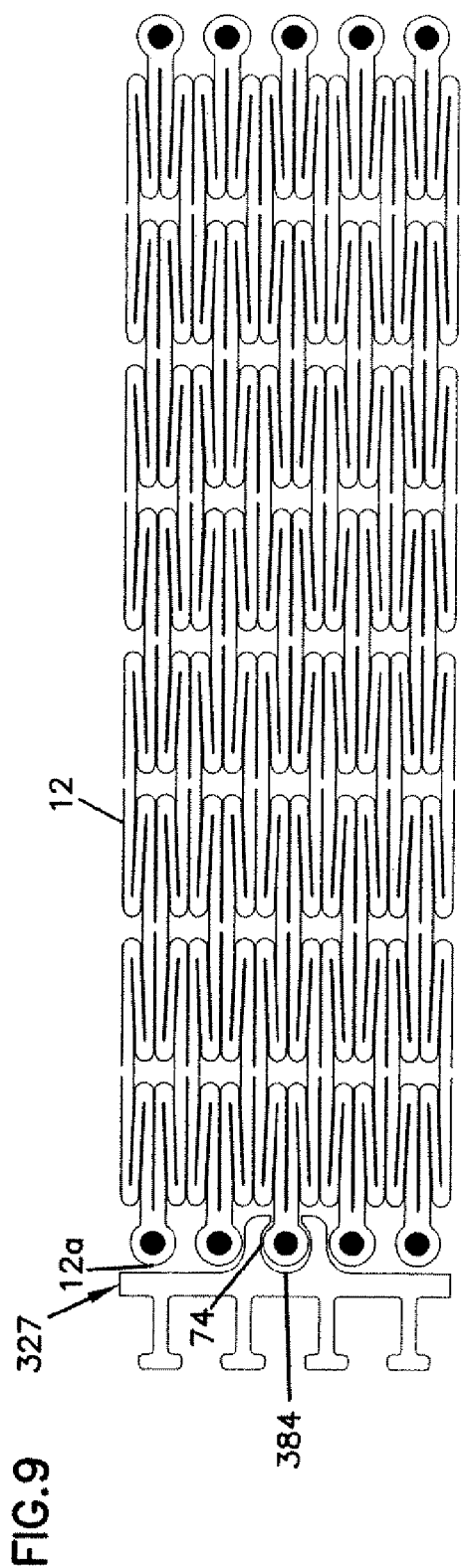

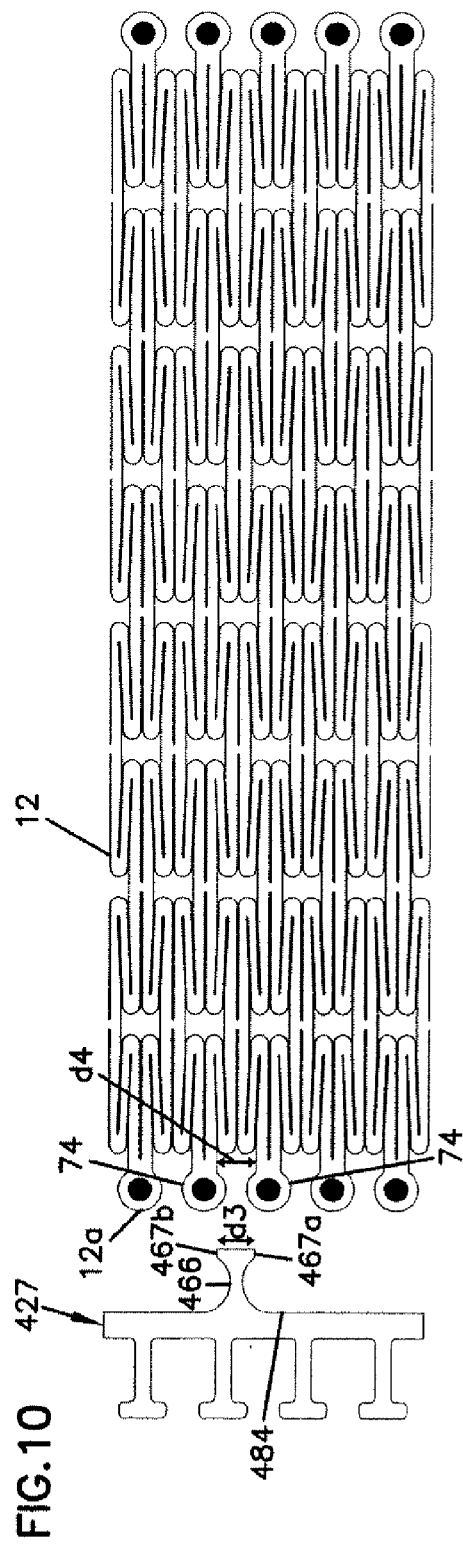
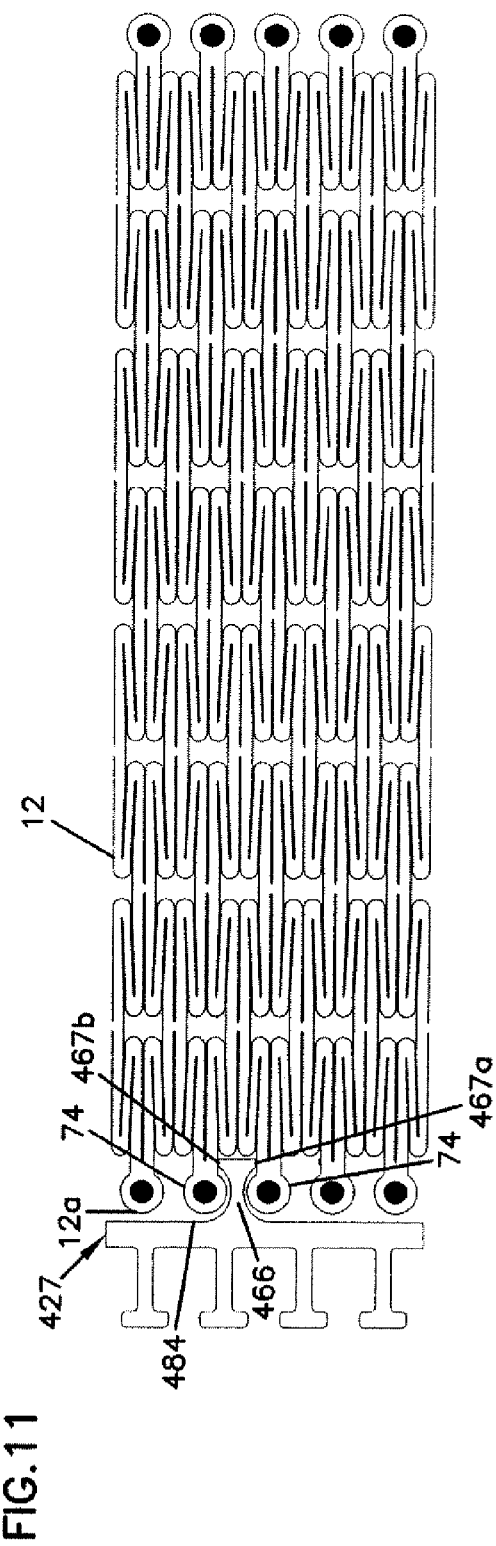
FIG.10
FIG.11

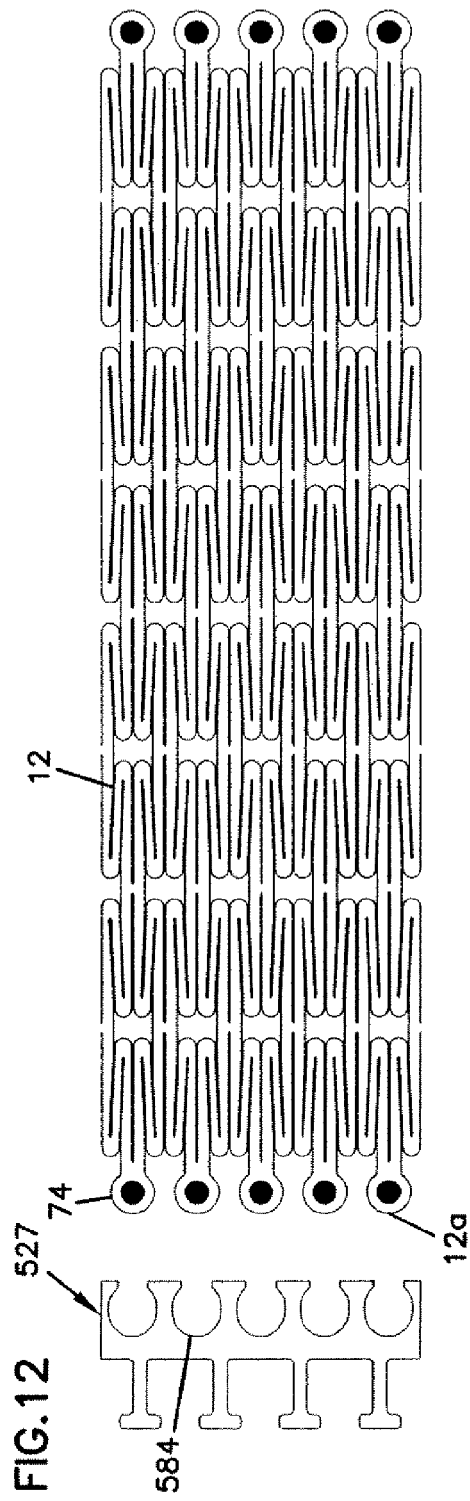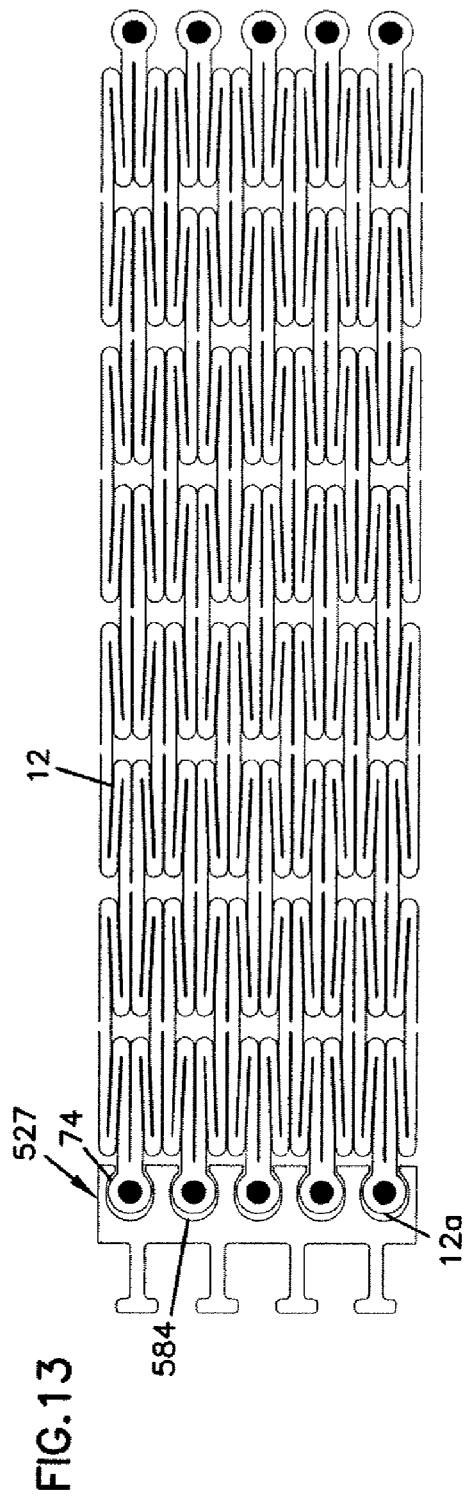

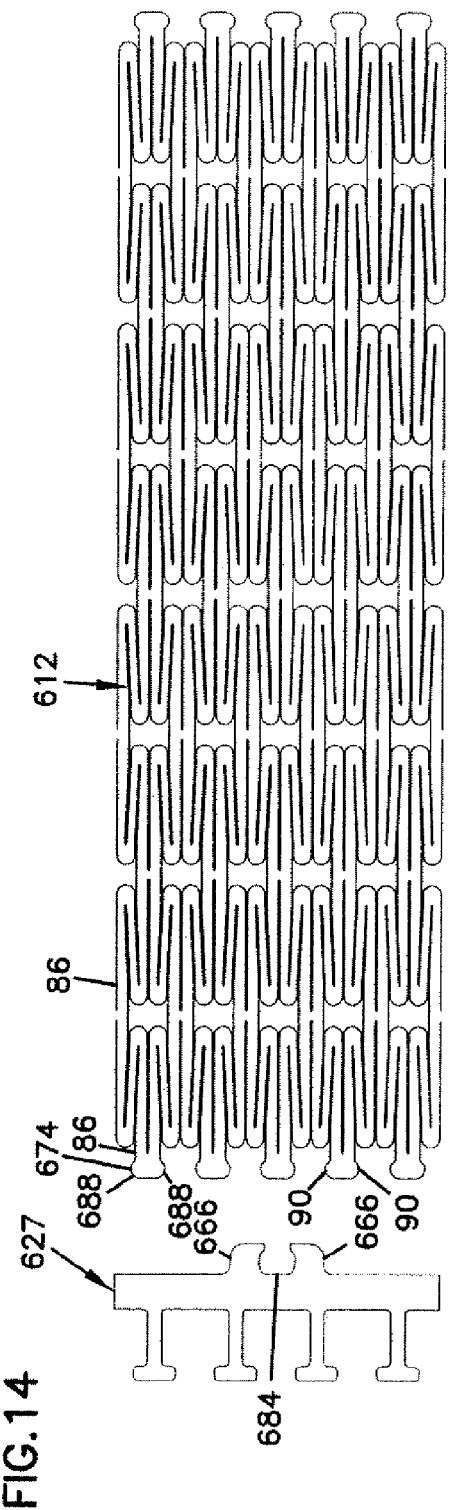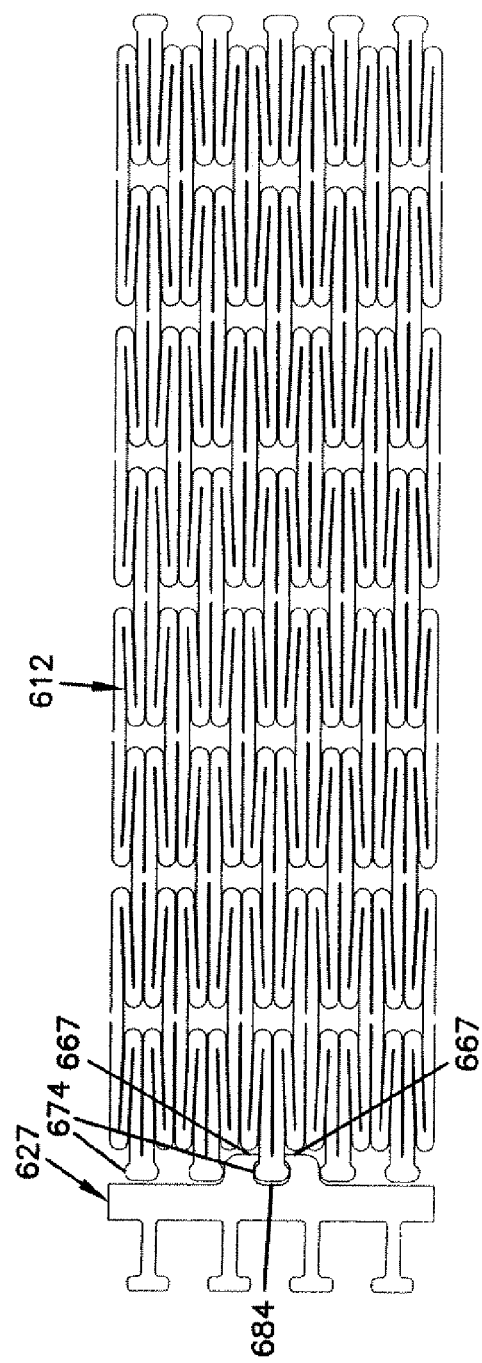

though the body lumen. The inner tube of the delivery system is hollow throughout its length such that it can be advanced over the guide wire to the deployment site.

IMPLANT DELIVERY SYSTEM WITH MARKER INTERLOCK

CROSS-REFERENCE TO RELATED APPLICATIONS

This application is a continuation of application Ser. No. 10/982,537, filed Nov. 4, 2004, now abandoned, which is a continuation of application Ser. No. 10/286,403, filed Nov. 1, 2002, which issued as U.S. Pat. No. 6,814,746, the entire contents of each of these applications being incorporated herein by reference.

TECHNICAL FIELD

This invention pertains to a system for delivering an implant to a site in a body lumen. More particularly, this invention pertains to a delivery system for a self-expandable implant such as a stent.

BACKGROUND

Stents are widely used for supporting a lumen structure in a patient's body. For example, stents may be used to maintain patency of a coronary artery, other blood vessels or other body lumen.

Stents are commonly metal, tubular structures. Stents are passed through a body lumen in a collapsed state. At the point of an obstruction or other deployment site in the body lumen, the stent is expanded to an expanded diameter to support the lumen at the deployment site.

In certain designs, stents are open-celled tubes that are expanded by inflatable balloons at the deployment site. This type of stent is often referred to as a "balloon expandable" stent. Other stents are so-called "self-expanding" stents. Self-expanding stents do not use balloons to cause the expansion of the stent. An example of a self-expanding stent is a tube (e.g., a coil tube or an open-celled tube) made of an elastically deformable material (e.g., a superelastic material such a nitinol). This type of stent is secured to a stent delivery device under tension in a collapsed state. At the deployment site, the stent is released so that internal tension within the stent causes the stent to self-expand to its enlarged diameter. Other self-expanding stents are made of so-called shape-memory metals. Such shape-memory stents experience a phase change at the elevated temperature of the human body. The phase change results in expansion from a collapsed state to an enlarged state.

A delivery technique for elastically deformable stents is to mount the collapsed stent on a distal end of a stent delivery system. Such a system would include an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout its length such that it can be advanced over the guide wire to the deployment site.

The combined structure (i.e., stent mounted on stent delivery system) is passed through the patient's lumen until the distal end of the delivery system arrives at the deployment site within the body lumen. The deployment system and/or the stent may include radiopaque markers to permit a physician to visualize positioning of the stent under fluoroscopy prior to deployment.

At the deployment site, the outer sheath is retracted to expose the stent. The exposed stent is now free to self-expand within the body lumen. Following expansion of the stent, the inner tube is free to pass through the stent such that the delivery system can be removed through the body lumen leaving the stent in place at the deployment site.

In prior art devices, the stent may prematurely deploy as the outer tube is retracted. Namely, with the outer tube partially retracted, the exposed portion of the stent may expand resulting in the remainder of the stent being squeezed out of the outer tube. This can result in the stent being propelled distally beyond a desired deployment site. Also, once the stent is partially unsheathed, it is sometimes determined that the stent placement needs to be adjusted. With existing systems, this is difficult since the stent has a tendency to force itself out of the sheath thereby making adjustments difficult. What is needed is a system that retains the stent on the catheter even when a majority of the stent has been exposed by retraction of the sheath, and allows a stent to be re-sheathed even after a majority of the stent has been exposed by retraction of the sheath.

Also, in existing systems, it is difficult to accurately determine the position of the stent. What is also needed is a system that provides an accurate visible indicator of the position of the stent.

SUMMARY

One aspect of the present disclosure relates to an implant delivery system that provides enhanced placement control of the implant.

Examples of a variety of inventive aspects are set forth in the description that follows. It is to be understood that both the foregoing general description and the following detailed description are exemplary and explanatory only and are not restrictive of the broad inventive aspects disclosed herein.

BRIEF DESCRIPTION OF THE DRAWINGS

FIG. 4 is a plan view of one embodiment of a stent having an interlock geometry that interlocks with an interlock structure of a delivery system, the stent and the interlock structure are shown cut longitudinally and laid flat with an axial separation between the stent proximal end and the mating interlock structure;

FIG. 5 is the view of FIG. 4 with the stent proximal end and mating interlock structure shown interlocked;

FIG. 8 is a plan view of the stent shown in FIG. 4 with a third embodiment of a mating interlock structure, the stent and the interlock structure are shown cut longitudinally and laid flat with an axial separation between the stent proximal end and the mating interlock structure;

FIG. 9 is the view of FIG. 8 with the stent proximal end and mating interlock structure shown interlocked;

FIG. 10 is a plan view of the stent shown in FIG. 4 with a fourth embodiment of a mating interlock structure, the stent and the interlock structure are shown cut longitudinally and laid flat with an axial separation between the stent proximal end and the mating interlock structure;

FIG. 11 is the view of FIG. 10 with the stent proximal end and mating interlock structure shown interlocked;

FIG. 12 is a plan view of the stent shown in FIG. 4 with a fifth embodiment of a mating interlock structure, the stent and the interlock structure are shown cut longitudinally and laid flat with an axial separation between the stent proximal end and the mating interlock structure;

FIG. 13 is the view of FIG. 12 with the stent proximal end and mating interlock structure shown interlocked;

FIG. 14 is a plan view of another embodiment of an alternative stent having an interlock structure that interlocks with an interlock structure of a six embodiment of a mating interlock structure, the stent and the interlock structure are shown cut longitudinally and laid flat with an axial separation between the stent proximal end and the mating interlock structure; and FIG. 15 is the view of FIG. 14 with the stent proximal end and mating interlock structure shown interlocked.

DETAILED DESCRIPTION

With reference now to the various drawing figures in which identical elements are numbered identically throughout, a description is provided of embodiments that are examples of how inventive aspects in accordance with the principles of the present invention may be practiced.

I. Delivery System

Figure 1:
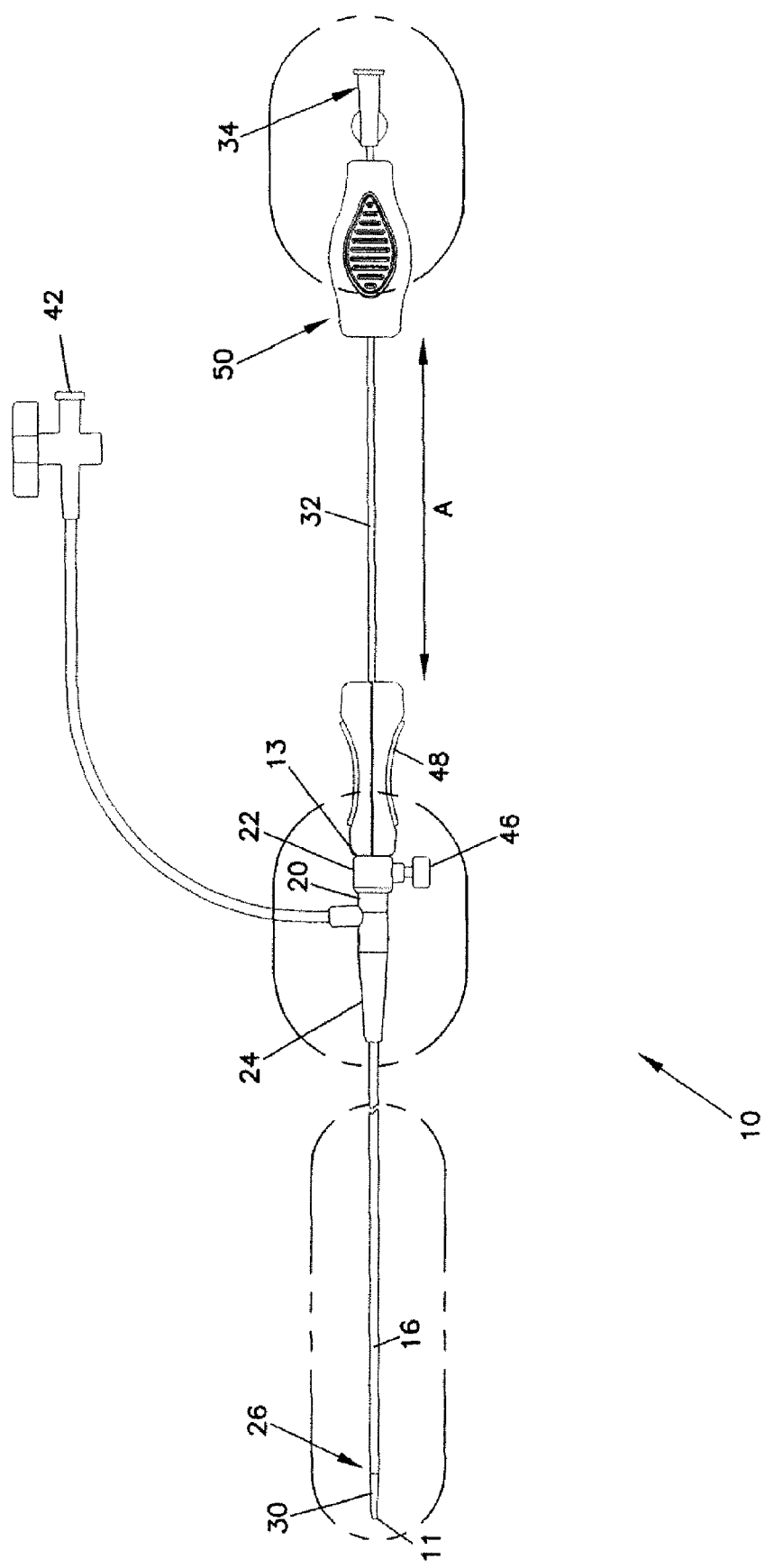
FIG. 1 is a side elevation view of one embodiment of a stent delivery system having features that are examples of inventive aspects in accordance with the principles of the present disclosure.
Figure 2:
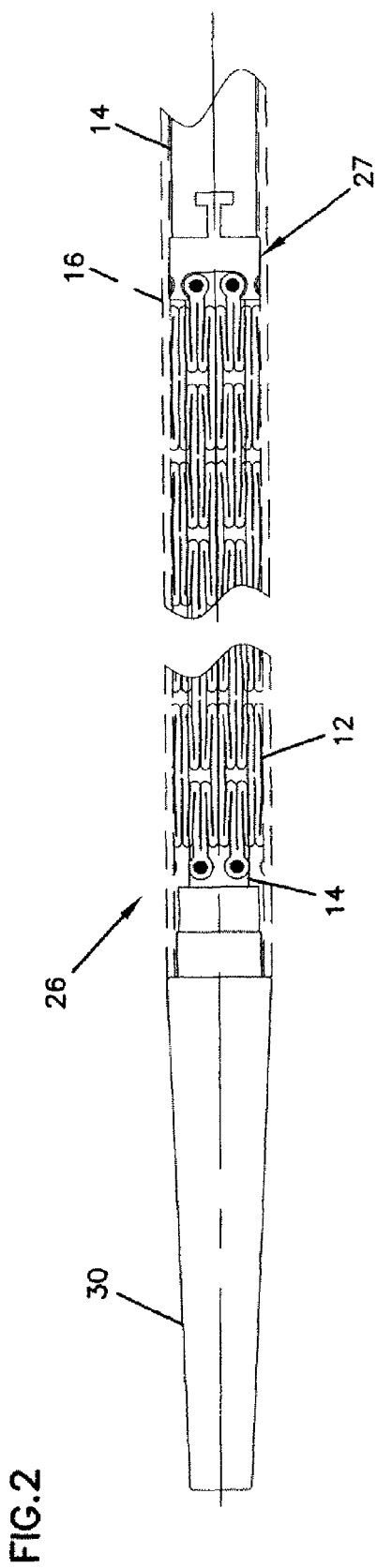
FIG. 2 is an enlarged view of the distal end of the system of FIG. 1 with an outer sheath shown in phantom line.
Figure 3:
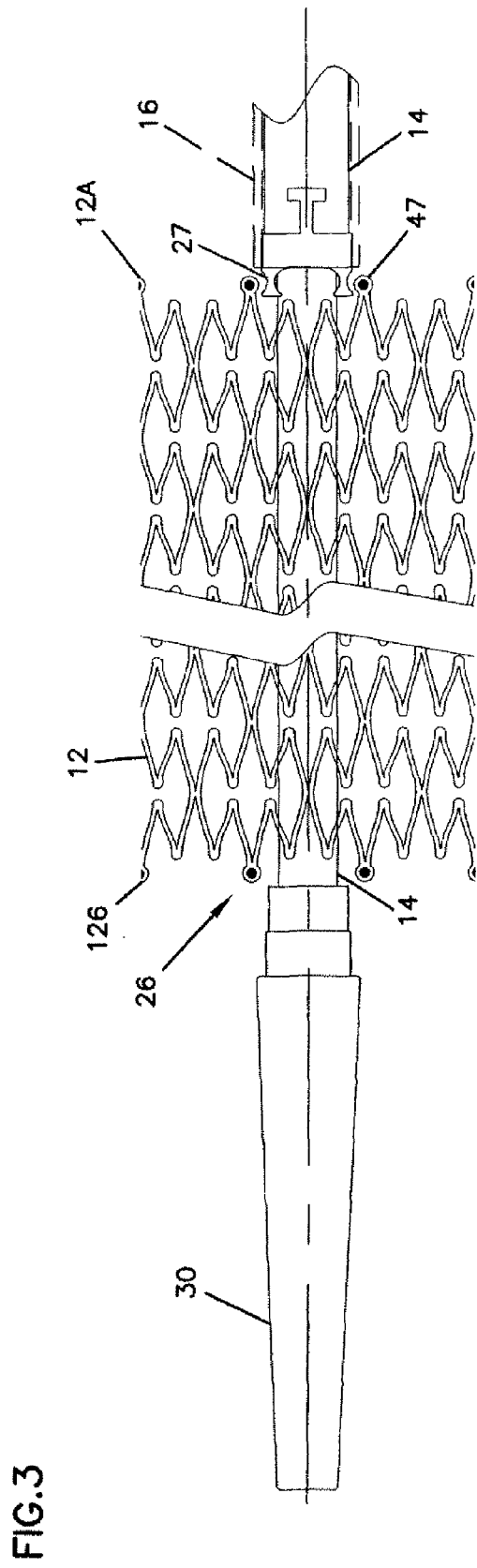
FIG. 3 is the view of FIG. 2 with the outer sheath retracted.

FIGS. 1-3 show a stent delivery system 10 having features that are examples of how certain inventive aspects in accordance with the principles of the present disclosure may be practiced. The system 10 has distal and proximal ends 11, 13, and includes an inner member 14 and a retractable outer sheath 16 that slides over the inner member 14. A stent mounting location 26 is located adjacent the distal end 11 of the system 10. A stent 12 (visible in FIGS. 2 and 3) is carried at the stent mounting location of the stent delivery system 10 in a collapsed (or reduced diameter) state. The stent 12 mounts over the inner member 14 and is covered by the sheath 16 so as to be retained in the collapsed state (see FIG. 2). The stent 12 is released (i.e., deployed) by retracting the sheath 16 to uncover or expose the stent 12 (see FIG. 3). The system 10 includes an interlock structure 27 that prevents the stent 12 from prematurely deploying. Upon release of the stent 12 from the stent delivery system 10, the stent 12 expands to an enlarged diameter to abut against the walls of the patient's lumen in order to support patency of the lumen. The expansion of the stent 12 also causes the stent 12 to disengage from the interlock structure 27.

The system 10 is sized to be advanced through the patient's body lumen. In use, the system 10 is preferably sufficiently long for the distal end 11 to be placed at the deployment site in the patient's body lumen with the proximal end 13 remaining external to the patient's body for manipulation by an operator.

The sheath 16 of the system 10 may have a variety of different constructions. In one embodiment, the sheath has a tubular construction of braid-reinforced polyester adapted to resist kinking and to transmit axial forces along the length of the sheath 16. The sheath 16 may be constructed so as to have varying degrees of flexibility along its length.

The inner member 14 of the system 10 is relatively flexible and can be made of a polymeric material such as nylon. In one embodiment, the inner member 14 has a tubular configuration and defines a lumen that extends through an entire length of the inner member 14. This type of configuration allows the system to be passed over a guidewire for guiding the system to a desired deployment location. However, in other embodiments, the inner member 14 can have a solid, non-tubular configuration.

The distal end 11 of the system 10 includes a tapered and flexible distal tip member 30 that is sufficiently flexible to permit advancement of the stent deployment system 10 through the patient's lumen while minimizing trauma to the walls of the patient's lumen. The tip 30 is connected to the inner member 14 adjacent the stent mounting location 26.

The proximal end 13 of the system 10 includes a manifold housing 20 connected to a lock housing 22. The sheath 16 connects to the manifold housing 20. A strain relief jacket 24 surrounds the sheath 16 adjacent its connection to the housing 20 to provide strain relief for the sheath 16. The inner member 14 passes through both the manifold housing 20 and lock housing 22. An outer reinforcing member 32 surrounds and is bonded to the inner member 14 adjacent the proximal end 13 of the system 10. The reinforcing member 32 is preferably made of a relatively rigid material such as stainless steel. A port housing 34 is bonded to the reinforcing member 32. The port housing 34 has a bore aligned with an inner lumen of the inner member 14 and functions to facilitate access to the inner lumen.

The manifold housing 20 carries an admission port 42 for injecting a contrast media into the interior of the manifold housing 20. The interior of the manifold housing 20 is preferably in fluid flow communication with a passage between the inner member 14 and the sheath 16. In use, the contrast media can be directed from the passage into the patient's body lumen through discharge ports (not shown).

The lock housing 22 carries a threaded locking member (or lock nut) 46 which can be turned to engage the reinforcing member 32. The lock nut 46 selectively permits and fixes axially movement between of the inner member and the sheath. Relative movement between the inner member and the sheath is permitted to define a transport position and a deploy position of the system 10.

First and second handles 48, 50 are secured to the lock housing 22 and reinforcing member 32, respectively. In the transport position, the handles 48, 50 are spaced apart and the sheath 16 covers the stent mounting location 26 to prevent premature deployment of the stent 12. When the handles 48 and 50 are moved toward each other, the sheath 16 slides rearwardly or proximally relative to the inner member 14. In other words, relative axial movement between the handles 48, 50 (represented by arrow A) results in relative axial movement between the inner member 14 and the sheath 16. In particular, the sheath 16 slides rearwardly from the transport position to the deploy position to fully expose the stent mounting location 26 and permit the stent 12 to freely expand toward its fully expanded diameter. After such expansion, the stent delivery system can be proximally withdrawn through the expanded stent and removed.

A stent delivery system is also described in U.S. patent application Ser. No. 09/954,555, filed Sep. 17, 2001, that is hereby incorporated by reference in its entirety.

II. Overview of Example Interlock Configurations

The stent delivery system 10 is adapted for delivery of a stent to a deployment site in a body lumen of a patient's body.

By way of non-limiting, representative example, the stent may be a self-expanding stent having a construction such as that shown in U.S. Pat. No. 6,132,461. In one non-limiting embodiment, the stent can be made of a superelastic metal such as nitinol, or the like. The stent may also be a coil stent or any other self-expanding stent. Another representative stent is shown in U.S. patent application Ser. No. 09/765,725, filed Jan. 18, 2001 and entitled STENT, which is hereby incorporated by reference. It is also contemplated that certain inventive aspects in accordance with the principles of the present invention are also applicable to balloon expandable stents. It will be appreciated that the inventive concepts disclosed herein are not limited to the particular stent configurations disclosed herein, but are instead applicable to any number of different stent configurations.

A concern with existing delivery systems for self-expanding stents is control of stent delivery. For example, due to their elastic characteristics, self-expanding stents have a tendency to propel themselves axially outwardly from their restraining sheaths before the sheaths have been completely retracted. When this occurs, control of stent placement is compromised since the stent may overshoot the desired deployment site. Further, once the stent has been completely deployed, subsequent adjustment of the stent deployment location can be difficult because re-sheathing typically cannot be readily accomplished.

To address the above concerns, the delivery system 10 is preferably equipped with an interlock configuration (e.g., interlock structure 27 of FIGS. 2 and 3) that constrains relative axial movement between the stent 12 and the inner member 14 until after the sheath 16 has been fully retracted. For example, when the stent 12 is mounted on the inner member 14 and restrained in the compressed orientation by the sheath 16, a first interlock geometry located at a proximal end 12a of the stent 12 interlocks with a second interlock geometry (e.g., interlock structure 27) adjacent the stent mounting location 26. The interlock geometries remain interlocked to constrain axial movement of the stent 12 until after the sheath has been retracted beyond a predetermined location (e.g., the proximal-most end 12a of the stent 12). When the sheath 16 has been retracted beyond the predetermined location, the interlock geometry of the stent 12 is allowed to expand. As the interlock geometry of the stent expands, the first interlock geometry of the stent 12 disengages from the second interlock geometry thereby allowing the inner member 14 of the system 10 to be moved axially relative to the stent without interference from the interlock geometries.

FIGS. 4-15 show 6 different interlock configurations. In each of the FIGS. 4-13, the stent 12 is depicted. In FIGS. 14 and 15, a modified stent 612 is depicted. In all of the FIGS. 4-15, proximal ends 12a, 612a of the respective stents 12, 612 are shown in relation to corresponding stent interlock structures (e.g., structures 27, 227, 327, 427, 527, 627). As can be understood, the stent interlock structures are located adjacent the stent mounting location 26 of stent delivery system 10. The structures 27, 227, 327, 427, 527 and 627 are preferably fixedly attached to the inner member 14 adjacent the mounting location 26. For example, the structures 27, 227, 327, 427, 527 and 627 can be bonded, crimped, swaged, affixed, fastened, fused, molded in, embedded in, or otherwise secured to the inner member 14. In each of the paired Figures (i.e. FIGS. 4-5, 6-7, 8-9, 10-11, 12-13 and 14-15), the stent and the stent interlock structure have been cut longitudinally and laid flat. In the first Figure of each pair (e.g. FIG. 4), the stent interlock structure and the stent are shown disengaged from one another. In the second Figure of each pair (e.g. FIG. 5), the stent interlock structure and the stent are shown interlocked.

In all FIGS. 4-15, the stents are depicted in the reduced diameter configuration. In all of FIGS. 4-15, the inner member 14 and the sheath 16 have been omitted for clarity.

While all of the embodiments depicted herein include stent retainers in the form of separate interlock pieces secured to the inner member 14, the invention is not so limited. For example, stent-retaining structures having interlocks can also be formed as an integral/unitary structure with the inner member.

III. Example Stent Configuration

Referring to FIGS. 4 and 5, the stent 12 of FIGS. 2 and 3 is depicted. The stent 12 has a length L and a circumference C, and includes a plurality of struts 86 (i.e., reinforcing members). At least some of the struts 86 have free terminal ends 72 that define proximal and distal ends 12a and 12b of the stent 12.

The stent 12 includes an interlock geometry in the form of enlargements 74 positioned at the free terminal ends of the struts 86. As shown in FIG. 4, the enlargements are circular enlargements. It will be appreciated that other shapes and interlock configurations could also be used. The enlargements 74 include interlock portions 88 that project outwardly from the struts 86 in a circumferential direction (i.e., in a direction coinciding with the circumference C of the stent 12).

In one embodiment, the stent 12 can be manufactured by cutting (e.g., laser cutting) the various features from a solid tube of material. When manufactured by this technique, the enlargements 74 do not project radially beyond an inner and outer diameter of the stent.

In the illustrated embodiment, the stent 12 includes radiopaque markers 18 that permit a physician to accurately determine the position of the stent 12 within the patient's lumen under fluoroscopic visualization. The markers 18 are preferably located adjacent the proximal and distal ends 12a, 12b of the stent. The markers 18 can be attached to the stent 12 by techniques such as adhesive, heat fusion, interference fit, fasteners, intermediate members or other techniques. Materials for making the radiopaque marker should have a density suitable for visualization through fluoroscopic techniques. Preferably, the markers have a radiopacity substantially greater than the material forming the struts of the stent. Exemplary materials comprise tantalum, platinum, gold, tungsten and alloys of such metals. In some embodiments, the markers can be coated with a radiopaque material or filled with a radiopaque filler.

In the illustrated embodiments shown in FIGS. 4-13, the markers 18 are at least partially defined at the interlock geometries located at the ends of the stent 12. In one embodiment, the enlargements 74 may define openings in the form of through-holes or through-apertures (i.e., holes that extend completely through the enlargements 74) within which the markers 18 may be positioned. For example, markers in the form of insert pieces can be press-fit or riveted within the through-holes. A process for mounting markers within through-holes is disclosed in U.S. patent application Ser. No. 10/286,355, entitled Method of Securing Radiopaque Markers to an Implant, filed on a date concurrent herewith, the application being incorporated herein by reference in its entirety. In another embodiment, the enlargements may include openings in the form of recesses (depressions that extend partially through the enlargements) within which the marker 18 may be placed. Positioning the markers 18 on the ends 12a, 12b of the stent 12 provides precise stent location information to a physician, even after deployment and removal of the stent delivery device.

IV. First Embodiment of Delivery System Interlock

Referring again to FIGS. 4 and 5, the interlock structure 27 of FIGS. 2 and 3 is depicted in isolation from the inner member 14 and the sheath 16. The interlock structure 27 includes a collar or band 68 the having a distal edge 29 facing the proximal end 12a of stent 12. Interlock structures in the form of receptacles 84 (i.e., sockets, openings, keyways, pockets, etc.) are defined adjacent the edge 29. The receptacles 84 are defined by partitions 66 that extend axially from the band 68. The partitions 66 each have a retaining structure 67 including extensions 67a, 67b that extend outwardly from the partitions 66 in opposite circumferential directions so as to partially enclose adjacent receptacles 84. The receptacles 84 are configured to receive the enlargements 74 of the stent 12.

The geometry of the receptacles 84 is selected to mate with the predetermined geometry of the stent proximal end 12a such that the stent 12 and the interlock structure 27 can be axially coupled or interlocked when the stent 12 is compressed at the mounting location 26. For example, similar to the enlargements 82, the receptacles 84 are shown having generally rounded or circular shapes. In the first embodiment shown in FIGS. 4 and 5, the receptacles 84 are each sized to receive and interlock with a pair of enlargements 74. When a pair of enlargements 74 are received within a receptacle 84, the extensions 67a, 67b of the retaining structures 67 oppose and circumferentially overlap the interlock portions 88 of the enlargement 74 (see FIG. 5) such that the stent is restricted from distal movement relative to the collar 27.

Each receptacle 84 defines an entrance opening 58 having first dimension d1 (FIG. 4) that extends between the corresponding extensions 67a, 67b. Outer edges of the struts 86 of the pair of male interlock structures 82 define a second dimension d2. In one embodiment, the first dimension d1 is less than the second dimension d2. Thus, when the stent 12 is interlocked with the interlock structure 27, the struts 86 corresponding to each pair of enlargements 74 are compressed together in a circumferential direction by contact with the extensions 67a, 67b of the retainers 67. Thus, the struts 86 corresponding to the same receptacle 84 are flexed together causing the enlargements 74 within the receptacle 84 to be moved closer together. Concurrently, struts 86 corresponding to adjacent receptacles 84 are flexed apart thereby widening a spacing between their corresponding enlargements 74. This occurs in part because retainers 67 have a dimension d3 that is larger than a dimension d4 between the struts 86. As shown in FIG. 3, when the structures 82 are flexed toward one another a visible gap G may be formed between the struts 86. By this configuration, the size of the enlargement 74 can be increased to accommodate larger sized markers 18 to assist in stent observation and placement. Without providing this configuration, increasing the size of the markers 18 would require lessening the material thickness of the partitions 66. In other embodiments, the receptacles can be sized to receive more than two enlargements.

With the specific embodiment shown, the stent 12 and interlock structure 27 are coupled such that the stent 12 and structure 27 are restricted from relative rotary motion (i.e., about axis X-X) and relative axial motion when the stent 12 is in the collapsed state. The predetermined stent geometry and the complementary mating geometry of the interlock structure 27 do not restrict relative radial motion. Namely, as the self-expanding stent 12 expands radially, the enlargements 74 are free to radially move out of the receptacles 84. After such motion, the stent 12 is no longer coupled to the interlock structure 27.

V. Second Embodiment of Delivery System Interlock

Figure 6:
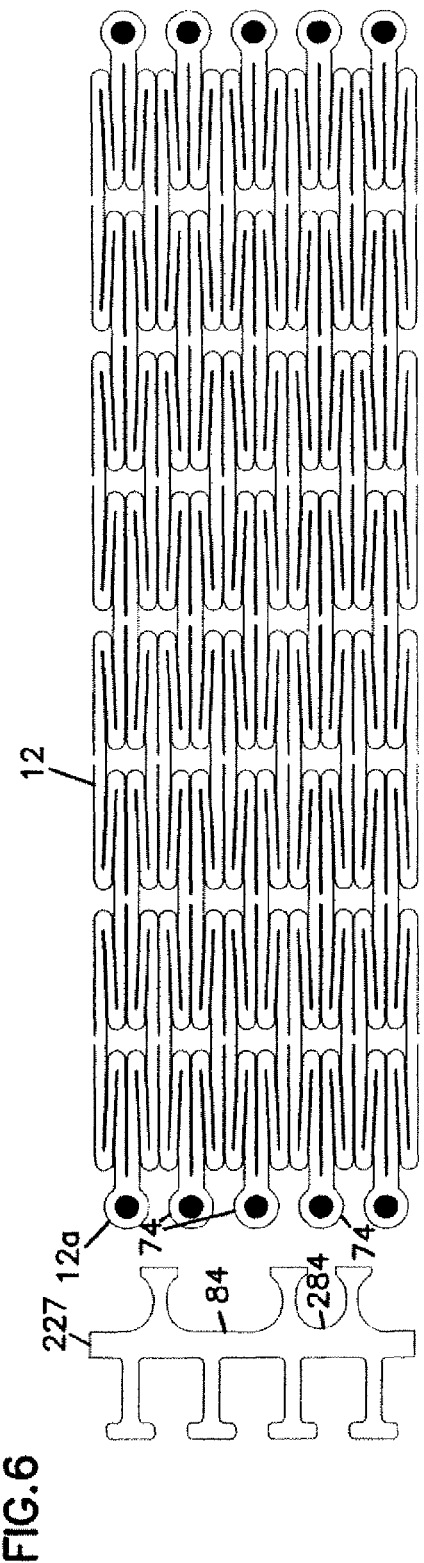
FIG. 6 is a plan view of the stent shown in FIG. 4 with a second embodiment of an interlock structure, the stent and the interlock structure are shown cut longitudinally and laid flat with an axial separation between the stent proximal end and the mating interlock structure.
Figure 7:
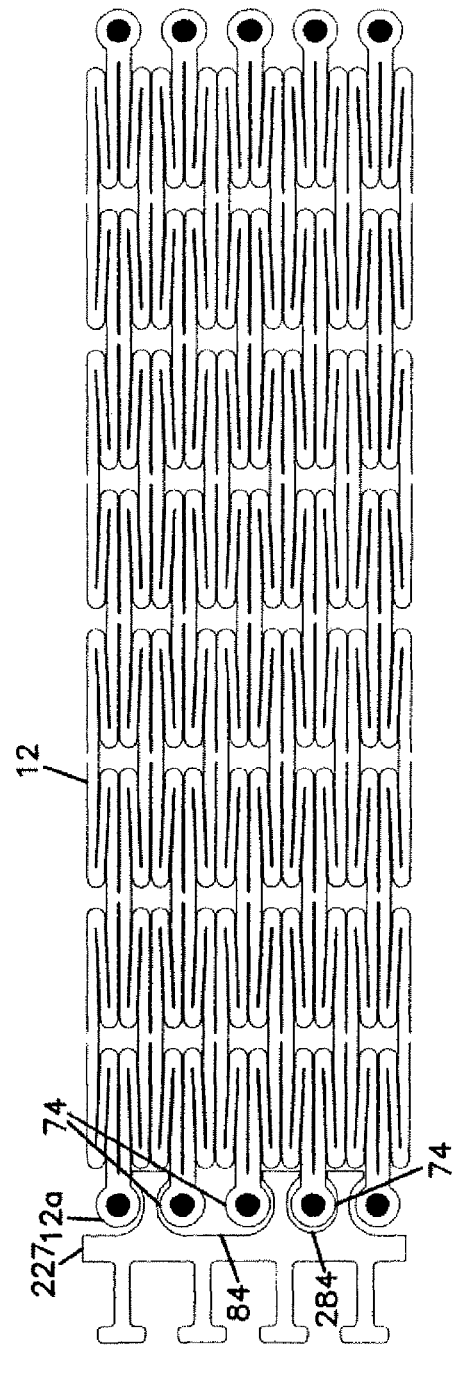
FIG. 7 is the view of FIG. 6 with the stent proximal end and mating interlock structure shown interlocked.

Referring now to FIGS. 6 and 7, a second interlock structure 227 adapted for use with the delivery system of FIGS. 1-3 is shown. Similar to the interlock structure 27, the interlock structure 227 is configured to interlock with the proximal end 12a of the stent 12. The interlock structure 227 includes receptacles 84 sized for receiving a pair of enlargements 74, and at least one receptacle 284 sized to receive a single enlargement 74. This type of embodiment is useful where a stent having an odd number of enlargements is used.

VI. Third Embodiment Of Delivery System Interlock

Referring now to FIGS. 8 and 9, a third interlock structure 327 adapted for use with the delivery system of FIGS. 1-3 is shown. Similar to the interlock structure 27, the interlock structure 327 is configured to interlock with the proximal end 12a of the stent 12. The interlock structure 327 defines a single receptacle 384 sized to receive and interlock with a single one of the plurality of enlargements 74.

In the illustrated embodiment of FIGS. 8 and 9, the receptacle 384 is defined by partitions 366 extending outward from a main band 368. The partitions 366 include only inward extensions 367, as no outward extensions are provided to define adjacent interlock structure. The partitions 366 can have a dimension d5 greater than a spacing d6 between the enlargements 74 to cause the enlargements 74 other that the one received in the receptacle 384 to be circumferentially compressed together when the pieces are interlocked. It is contemplated that other embodiments can include more than one receptacle 384 defined by partitions 366 having only inward extensions 367.

VII. Fourth Embodiment of Delivery System Interlock

Referring now to FIGS. 10 and 11, a fourth interlock structure 427 adapted for use with the delivery system of FIGS. 1-3 is shown. Similar to the interlock structure 27, the interlock structure 427 is configured to interlock with the proximal end 12a of the stent 12. The interlock structure 427 includes an interlock member 466 that interlocks between a pair of enlargements 74 of the stent 12. The interlock member 466 defines a single receptacle 484 that receives all of the enlargements 74 of the stent 12.

In the embodiment of FIGS. 10 and 11, the member 466 has a first extension 467a and a second extension 467b. The extensions 467a, 467b of the interlock member 466 function to oppose and circumferentially overlap portions of the enlargements 74 (see FIG. 11) to restrict distal movement of the stent 12 relative to the interlock structure 427. The member 466 defines a dimension d3 greater than a dimension d4 between the struts. This variance in dimensions causes at least some of the enlargements 74 to be compressed together in a circumferential direction within the receptacle 484.

VIII. Fifth Embodiment of Delivery System Interlock

Referring now to FIGS. 12 and 13, a fifth interlock structure 527 adapted for use with the delivery system of FIGS. 1-3 is shown. Similar to the interlock structure 27, the interlock structure 527 is configured to interlock with the proximal end 12a of the stent 12. The interlock structure 527 includes receptacles 584 corresponding to each of the enlargements 74 of the stent 12. Each receptacle 584 is sized to receive a single one of the enlargements 74.

IX. Sixth Embodiment of Delivery System Interlock

Referring now to FIGS. 14 and 15, a sixth interlock structure 627 adapted for use with the delivery system of FIGS. 1-3 is shown. The interlock structure 627 is adapted to interlock with enlargements 674 of an alternative stent 612. In the illustrated embodiment of FIGS. 14 and 15, the enlargements 674 are in the form of oblong projections. The oblong projections include interlock portions 688 that project outwardly from struts 86 in a circumferential direction (i.e., in a direction coinciding with the circumference C of the stent 612). The interlock portions 688 include interlock surfaces 690 that face in a distal direction. Unlike the previous stent 12 embodiment, the stent 612 does not include markers at the enlargements 674.

The interlock structure 627 defines a receptacle 684 sized to receive a single enlargement 674. The receptacle 684 is defined by partitions 666 having only inward extensions 667. When interlocked, the extensions 667 oppose and circumferentially overlap the interlock surfaces 490 of the enlargements 474 (see FIG. 15). Thus, the stent is restricted from distal movement relative to the interlock structure 627 when the two components are interlocked.

It is contemplated that more than one of the receptacles 684 can be used. Further, it is also contemplated that the partitions 666 can include outward extensions to define adjacent receptacles having the oblong configuration. Moreover, similar to at least some of the previous embodiments, the partitions 666 can have a dimension thicker that a corresponding dimension between the struts 86 to cause at least some of the enlargements 674 to be compressed together in a circumferential direction when the stent 12 and the interlock structure 627 are interlocked.

X. Other Embodiments

The depicted embodiments show that the interlock between the stent 12 and the inner member 14 is provided at the proximal end 12a of the stent 12. It will be appreciated that for certain embodiments, the interlock between the inner member 14 and the stent 12 can be provided at the distal end 12b of the stent 12 (e.g., for a distally retractable sheath). Moreover, while the embodiments shows interlock structures (e.g., enlargements) provided at all of the proximal ends of the struts 86, the invention is not so limited. For example, in some embodiments, only some of the struts 86 may include interlock structures.

While the various embodiments of the present invention have related to stents and stent delivery systems, the scope of the present invention is not so limited. For example, while particularly suited for stent delivery systems, it will be appreciated that the various aspects of the present invention are also applicable to systems for delivering other types of self-expandable implants. By way of non-limiting example, other types of self-expanding implants include anastomosis devices, blood filters, grafts, vena cava filters, percutaneous valves, or other devices.

It has been shown how the objects of the invention have been attained in a preferred manner. Modifications and equivalents of the disclosed concepts are intended to be included within the scope of the claims.

What is claimed is:

1. A medical device for implanting an implant at a deployment location, comprising:
    an implant including a plurality of struts having terminal ends, at least some of the terminal ends of the struts including a plurality of first interlock structures, and
    an implant delivery system including an inner member and an outer sheath slideably disposed over the inner member, the delivery system including an implant mounting location at which the implant mounts, the outer sheath being movable from a transport position where the sheath covers the implant at the implant mounting location, to a deploy position where the implant is exposed, the implant delivery system further including two or more second interlock structures, exactly two adjacent second interlock structures define a single receptacle therebetween, and wherein an outer periphery of at least two of the first interlock structures are disposed at least partially within the same receptacle to prevent deployment of the implant while the first and second interlock structures are engaged.

2. The medical device of claim 1, wherein the first interlock structure comprises multiple enlargements that are circumferentially compressed together within the same receptacle.

3. The medical device of claim 1, wherein the implant is a balloon-expandable implant.

4. A medical device for implanting an implant at a deployment location, comprising:
    an implant including a plurality of struts having terminal ends, at least some of the terminal ends of the struts including a plurality of first interlock structures, and
    an implant delivery system including an inner member and an outer sheath slideably disposed over the inner member, the delivery system including an implant mounting location at which the implant mounts, the outer sheath being movable from a transport position where the sheath covers the implant at the implant mounting location, to a deploy position where the implant is exposed, the implant delivery system further including two or more second interlock structures, exactly two adjacent second interlock structures define a single receptacle therebetween, wherein exactly two of the first interlock structures are at least partially disposed within the receptacle to prevent deployment of the implant while the first and second interlock structures are engaged.

5. The medical device of claim 4, wherein the first interlock structures comprise enlargements, and wherein exactly two adjacent second interlock structures receive at least two adjacent enlargements therebetween.

6. The medical device of claim 4, wherein the implant is a balloon-expandable implant.

7. A medical device for implanting an implant at a deployment location, comprising:
    an implant including a plurality of struts having terminal ends, at least some of the terminal ends of the struts including a plurality of first interlock structures, and
    an implant delivery system including an inner member and an outer sheath slideably disposed over the inner member, the delivery system including an implant mounting location at which the implant mounts, the outer sheath being movable from a transport position where the sheath covers the implant at the implant mounting location, to a deploy position where the implant is exposed, the implant delivery system further including two or more second interlock structures, exactly two adjacent second interlock structures define one receptacle therebetween, wherein the receptacle houses an outer periphery of at least two of the first interlock structures to prevent deployment of the implant while the first and second interlock structures are engaged.

8. The medical device of claim 7, wherein the first interlock structures comprise enlargements, and wherein the enlargements extend radially outward from points of intersection between the strut and the enlargement.

9. The medical device of claim 7, wherein an inner, concave surface of the second interlock structures engages an outer, convex surface of the first interlock structures.

10. The medical device of claim 7, wherein the implant is a balloon-expandable implant.

* * * * *